United States Patent [19]

Ruggieri et al.

[11] Patent Number: 5,688,970
[45] Date of Patent: Nov. 18, 1997

[54] PROCESS TO RECYCLE EXHAUST GASES FROM N-BUTANE CONVERSION INTO MALEIC ANHYDRIDE

[75] Inventors: Roberto Ruggieri, Milan; Salvatore Cassarino, Rome, both of Italy

[73] Assignee: Sisas Societa' Italiana Serie Acetica E Sintetica SpA, Milan, Italy

[21] Appl. No.: 395,438

[22] Filed: Feb. 28, 1995

[30] Foreign Application Priority Data

Jun. 30, 1994 [IT] Italy .................. MI94A1359

[51] Int. Cl.$^6$ .................. C07D 307/60
[52] U.S. Cl. .................. 549/262
[58] Field of Search .................. 549/262

[56] References Cited

U.S. PATENT DOCUMENTS

| | | | |
|---|---|---|---|
| 3,891,680 | 6/1975 | Katsumoto et la. | 260/346.8 M |
| 4,231,943 | 11/1980 | Paradis et al. | 260/346.75 |
| 4,259,246 | 3/1981 | Bakshi etal. | 260/346.75 |
| 5,069,687 | 12/1991 | Bertola et al. | 55/44 |

FOREIGN PATENT DOCUMENTS

| | | | |
|---|---|---|---|
| 0 099 431 | 2/1984 | European Pat. Off. | C07D 307/60 |
| 0 546 677 A1 | 6/1993 | European Pat. Off. | |

*Primary Examiner*—Margaret W. Glass
*Attorney, Agent, or Firm*—Nixon & Vanderhye

[57] ABSTRACT

In producing maleic anhydride by catalytic oxidation of butane in vapor phase, the reaction mixture consists of butane and a recycle gaseous current made of compressed air and exhaust gas recovered from the absorption stage by a solvent of the maleic anhydride produced; oxygen and total butane concentration in the recycle stream are controlled.

13 Claims, 1 Drawing Sheet

PROCESS TO RECYCLE EXHAUST GASES FROM N-BUTANE CONVERSION INTO MALEIC ANHYDRIDE

This invention concerns production of maleic anhydride by catalytic oxidation of butane in vapour phase.

This reaction takes place in a longitudinal flow pipe reactor containing a fixed bed of catalysts having different reactivity degrees.

Air is typically used as the oxidizing agent; however, the process can use enriched air or oxygen.

BACKGROUND OF THE INVENTION

In the reactor, alongside the conversion reaction of butane into maleic anhydride:

$$C_4H_{10}+3.5O_2 \rightarrow C_4H_2O_3+4H_2O$$

other secondary reactions take place, among which the main ones are butane combustion reactions forming carbon monoxide and carbon dioxide:

$$C_4H_{10}+4.5O_2 \rightarrow 4CO+5H_2O$$

$$C_4H_{10}+6.5O_2 \rightarrow 4CO_2+5H_2O.$$

Reactions are strongly exothermic and reaction heat is suitably removed by circulating—in the reaction section external to the reaction pipes—a coolant (usually molten salts) which thereafter release heat to a steam generator.

Conversion, selectivity and reaction yield depend on reaction conditions, mainly on feed composition, pressure, temperature and space velocity (this latter measured as standard volume of gas fed per hour per catalyst volume unit).

Typically, conversion varies from 75 to 90%; selectivity, from 55 to 75%.

By conversion is meant the butane percentage in weight fed to the reactor, which is transformed into a product or by-products.

By selectivity is meant the amount of maleic anhydride expressed as the converted butane percentage in weight.

The conversion product by selectivity determines yield, which identifies the amount of maleic anhydride produced, expressed as total butane percentage in weight fed to the reactor.

Non-converted butane is present in the reaction effluent.

The maleic anhydride produced is recovered by selective absorption of maleic anhydride from reaction gases by means of an absorption medium which may be water or, preferably, a selective organic solvent for instance preferable chosen among diesters of phthalic acid such as dibutyl phthalate and dioctyl phthalate.

Conventionally, absorption is carried out at a pressure which is slightly higher than atmospheric pressure, sufficient to ensure exhaust gas transfer to an incinerator where organic compounds (mostly butane) are burnt and, after recovering heat, are exhausted into the atmosphere.

The result is that non-converted butane prejudices process in terms both of yield, therefore higher raw material costs, and of higher release of carbon dioxide into the air.

In order to increase yield, a fraction of the exhaust gases may be taken into consideration for recycling to the reaction.

Recycling of exhaust gases—containing non-converted raw materials—is a well-known procedure which has been used in various industrial processes, including catalytic oxidation in vapour phase.

For example, this procedure is normally used in catalytic oxidation of ethylene to ethylene oxide.

In the area of maleic anhydride production from butane, recycling of reaction gas is reported in Bissot and Benson's article "Oxidation of Butane to Maleic Anhydride", pages 57–60, Industrial Engineering Chemistry, Book 2, no. 1, March 1963.

However, the article describes recycling within a process including a number of series-connected reactors with maleic anhydride separation between reactors.

This process received no industrial interest because of its complexity and high investments.

Recycling was also reported in a number of patents (such as U.S. Pat. No. 3,899,516, U.S. Pat. No. 3,904,652, U.S. Pat. No. 4,222,945, U.S. Pat. No. 4,342,699, U.S. Pat. No. 5,011,945), all of them featuring use of oxygen or enriched air as oxidizing medium.

In all processes using oxygen, exhaust gas recycling to the reaction is an essential factor it being anyhow necessary to dilute oxygen and prevent explosion hazards.

Moreover, these processes are characterized by operating conditions which remarkably differ from processes using air.

A typical use is high butane charge concentrations, obtaining low conversions per pass, so as to limit formation of gaseous by-products such as carbon monoxide and carbon dioxide which should be removed by releasing a fraction of exhaust gases.

Since exhaust gases in processes using oxygen contain high butane concentrations, even a relatively low release would heavily cut yield.

Moreover, use of oxygen instead of air tends to prejudice process profitability due to operating and investment costs of the oxygen production unit.

U.S. Pat. No. 4,231,943 reports exhaust gas recycling combined with use of air as oxidizing medium.

The process described in this latter patent is inspired by principles which are typical of processes based on use of oxygen, i.e. low butane conversions per pass (typically, 20 to 28%), relatively high concentration of butane in the feed (2 to 4%) and low oxygen feed concentration.

Process chemistry shows that—even under optimum conditions—when using air at least 4 tons of inert gas (nitrogen) should be released per ton of maleic anhydride produced.

Considering the high inlet and outlet butane concentrations with regard to the reactor, this operation involves very high butane losses in the released products.

To prevent this, U.S. Pat. No. 4,231,943 provides a unit to remove butane from released gases by absorption on activated carbon.

Butane absorption by activated carbon—from large gas deliveries to be treated at low pressure—is complicated and requires very high and costly amounts of absorbing medium.

DESCRIPTION OF THE INVENTION

Therefore, the main objective of this invention is providing a process to produce maleic anhydride where the above-mentioned problems and troubles are substantially removed in an industrially convenient manner.

According to this invention, the objective is attained through a process to produce maleic anhydride by catalytic oxidation in vapour phase of n-butane, where the oxidizing medium is a mixture of air—or, as an alternative, enriched air, or oxygen —and recycled reaction gases, characterized by the following operations:

(a) Preparing of the reaction mixture consisting of a butane charge and a recycle gaseous stream, this gaseous stream including:

(i) Compressed air at a pressure of 2.03 bar at least;

(ii) Recovered exhaust gas, compressed at a pressure of 1.21 bar at least; the percentage of the said exhaust gas (ii) in such recycle stream being regulated so that oxygen concentration in the reaction mixture ranges from 10% to 18% by volume, and the amount of charged butane being in turn regulated so that total butane concentration in the reaction mixture ranges from 1.6% to 3.0% by volume.

(b) Feeding reaction mixture to an oxidation reactor where a known catalyst causes butane to react producing high conversion per pass and high selectivity.

(c) Cooling of reaction gases comprising nitrogen, oxygen, non-converted butane, organic by-products, water steam and maleic anhydride produced.

(d) Recovering maleic anhydride by absorption in a solvent selected among water and selective organic solvents, at a gas pressure on absorption stage outlet ranging from 1.21 and 3.04 bar.

(e) Water-scrubbing of an exhaust gas fraction after removal of maleic anhydride, so as to eliminate all organic compounds present, excepting butane, to produce the said recovery exhaust gas to be recycled.

(f) Conveying the remaining exhaust gas fraction to an incinerator where butane and organic by-products in the exhaust gases are burnt and produce water and carbon dioxide.

The typical reaction-with-recycle conditions that are the subject of this invention, are shown in the Table 1 hereinbelow, where column A describes the variation range of each parameter, and column B the preferred value:

|  | A | B |
|---|---|---|
| Reaction temperature (°C.) | 370–440 | 400 |
| Reactor inlet pressure (bar) | 2.03–6.08 | 3.44 |
| Space velocity ($h^{-1}$) | 1000–3000 | 1500 |
| Total butane concentration fed to reactor (% volume) | 1.6–3.0 | 2.1 |
| % oxygen in the feed to reactor (% vol) | 11–16 | 12.2 |
| Total yield (kgs of maleic anhydride per kg of butane) | 0.9–1.05 | 1.03 |

When operating a reaction by the same operating parameters in column B, however without recycle, it was found that yield drops from 1.03 to about 0.94 Kg of maleic anhydride per kg of butane.

This is due to two main factors:

a) By the process described in this invention, the butane share in the exhaust gases recycled to the reactor, is recovered to the reaction.

b) The mixture charged, consisting of water and recycling gas, contains oxygen typically ranging from 10 to 18% by volume, preferably 11 to 14%, however remarkably lower than air (21% by volume).

When using suitable catalysts optimized to work under recycling conditions, it was found that the lower oxygen concentration allows better control on temperature peaks during reaction (hot spots), and consequently higher selectivity.

Preferred catalysts to be used in the process described in this invention are high specific surface and high activity type, so as to allow quick development of reaction also when oxygen is available in reduced amounts, without excessively increasing reaction temperature to the detriment of selectivity. Among preferred catalysts, phosphorous and vanadium-based types whose formulae are $V_x P_y O_z$ (e.g. pyrophosphate vanadyl), having proper crystal structures with large specific surfaces. As regards the advantages arising from this invention, we can quote high butane conversion per pass, typically ranging from 75 to 90%, and high conversion selectivity, usually ranging from 55 to 75%.

Best selectivity and yield (consequently less butane consumption) are not the only advantage offered by the process which also allows less consumption of electric power and improved environment-friendly features.

One of the advantages offered by this process actually is electric power saving.

Comparing a typical case (Column B in Table I) and an identical case without recycling, saving on operating costs—in terms of compression energy—is about 30% for the benefit of process with recycle, feed butane concentration being equal.

This is due to the lower compression ratio required for compressing recycle gas from a high-averaging pressure (typically 1.21 to 3.04 bar) to the reaction pressure (typically 2.03 to 6.08 bar), over an equivalent air volume available at atmospheric pressure.

This is, in absolute terms, an important saving which in an optimized project can exceed 300 Kwh per ton of maleic anhydride produced.

As regards impact on the environment by the traditional technology, the exhaust gas —after selective absorption of maleic anhydride—is conveyed to an incinerator where residual organic compounds (mainly butane) are burnt.

Incinerator effluents do not contain organic compounds, fully converted into carbon dioxide and water steam.

By the technology described in this invention, only a fraction of the gaseous effluent is conveyed to the incinerator.

This offers the following advantages:

Remarkably reduced dimensions of incinerator;

Remarkable reduction in carbon dioxide release into the air.

From comparison of the typical case in Column B (Table I) and an identical case without recycle, a reduction in butane conveyed to the incinerator i.e. about 90 Kg butane per ton of maleic anhydride produced, is found.

This means a reduction of about 270 Kg of carbon dioxide released into the air per ton of maleic anhydride produced.

Benefits to the environment are obvious, and can be assessed as less carbon dioxide (thousand of tons/year) released by plants, including low or medium-capacity facilities.

These benefits are greater vs. other technologies which offer lower yields, typically ranging from 0.80 to 0.85 tons of maleic anhydride produced per one ton of butane/fed.

DESCRIPTION OF THE DRAWINGS

The invention will now be described with reference to the accompanying drawings, in which.

DESCRIPTION OF PREFERRED EMBODIMENTS

Figure 1:
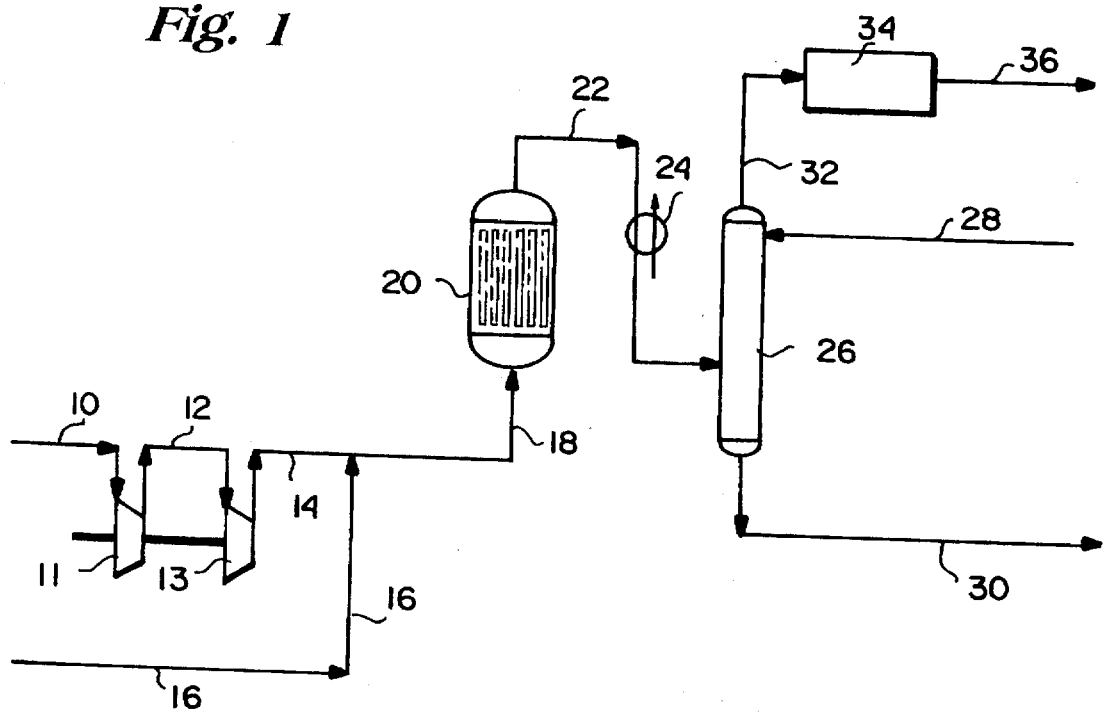
FIG. 1 shows schematically a plant for traditional processing without recycle.

Referring to FIG. 1, the air is fed (line 10) to the 1st stage (11) of a compressor, to be compressed (line 12) to a pressure ranging from 1.21 to 3.04 bar, then fed to a second compression stage (13).

When exiting the second compression stage, the compressed air (line 14) blends with the butane feed (line 16) at a pressure ranging from 2.03 to 6.08 bar.

The mixture thus obtained (line 18) is fed to reactor (20), preferably of the longitudinal flow fixed bed type, even though the features of this invention allow application to other types of reactors, for example fluidized-bed reactors.

By means of a suitable catalyst, butane is oxidized to maleic anhydride and by-products in the reactor (20). Reaction temperature usually ranges from 380° to 440° C.

Effluent gas from reactor comprises nitrogen, residual oxygen, non-converted butane, maleic anhydride and reaction by-products.

Reaction by-products are carbon monoxide, carbon dioxide and organic compounds such as acetic acid and acrylic acid.

Effluent gases from reactor (line 22) are cooled in unit (24) and conveyed to an absorber (26) where maleic anhydride produced is recovered, operating at a low outlet pressure (usually lower than 1.21 bar).

The absorber (26) preferably uses an organic solvent (line 28) as absorbing medium, or even better a solvent as described in U.S. Pat. No. 5,069,687.

The exhaust solvent (line 30) feeds a maleic anhydride recovery unit of the type described in the above patent.

The process finds application even when water is used as absorbing medium.

After maleic anhydride absorption, the exhaust gases are conveyed (line 32) to an incinerator (34); from here, they are released into the air (line 36).

Figure 2:
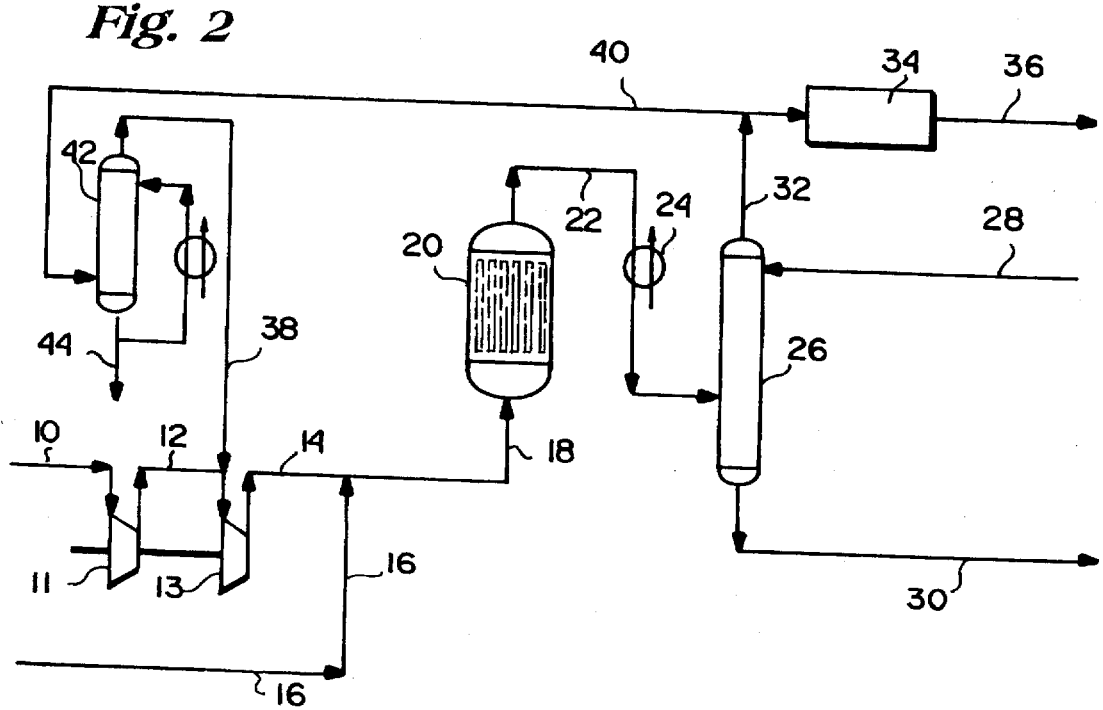
FIG. 2 shows schematically a plant employed for the present invention.

Referring to FIG. 2 (scheme), concerning the invention herein, the description hereinafter lists the components that are identical or equivalent to those in FIG. 1, using the same references as far as possible.

Here, air is fed (line 10) to the first stage (11) of compressor, to be compressed to a pressure ranging from 1.21 to 3.04 bar.

At this pressure the air is mixed with recycle gas (line 38) to produce a mixture which is conveyed to the second stage (13) of compressor where it is compressed at a pressure ranging from 2.03 to 6.08 bar.

When exiting the second compression stage, the mixture (line 14) joins butane feed (line 16), producing a charge mixture (18) which feeds the reactor (20), designed and operating as described with respect to FIG. 1.

After cooling in unit (24), the effluent gases (22) from reactor (20) are conveyed to the absorber (26)—identical to absorber in FIG. 1 except for the features described hereinbelow.

Unlike the traditional technique, where the absorber operates at an outlet gas pressure slightly higher than atmospheric pressure (typically lower than 1.21 bar), the technique described in this invention uses the absorber preferably—but not necessarily—at higher outlet pressures, usually ranging from 1.21 to 3.04 bar.

Here, after maleic anhydride absorption, exhaust gases (32) divide into two fractions i.e. one fraction (40) as recycle gas and one fraction conveyed to the incinerator (34).

The recycle gas (40) is fed to a traditional water-scrubbing column (42), where water-soluble organic compounds are separated in the form of condensate (44).

Since butane in the recycle gas is insoluble, it is retained by gas after scrubbing and is fed (line 38) to the second compression stage suction.

As evidenced by comparing FIGS. 1 and 2, the plant for the present invention includes a recycling line (line 40 FIG. 2), recycle gas scrubbing column (42) and scrubbed recycle gas line (line 38 FIG. 2) which feeds the interstage of charge compressor.

The advantages offered by this invention are evidenced by the two examples hereinafter wherein example 1 describes a process where exhaust gases are recycled according to this invention. Example 2 describes a process without recycle gas according to the traditional technique.

The two examples are referred to a plant having identical output capacity, with fixed-bed reactors of identical dimensions.

EXAMPLE 1

With reference to FIG. 2 annexed hereto, the process with gas recycling is as follows:

35,693 Kg/h of air are fed (line 10) to 1st compression stage suction (11).

On 1st stage delivery, the air (line 12)—at a pressure of 2.03 bar—is mixed with 38,720 Kg/h of recycle gas (line 38) from a scrubbing column (42).

This mixture is fed to the second compression stage (13) to be compressed to a 3.55 bar pressure, subsequently mixed with 3,008 Kg/h of n-butane feed (line 16).

The total mixture (line 18) is the feed to the reactor (20). The feed is 77,421 Kg/h and consists of:

| | |
|---|---|
| Oxygen | 12.2% by volume |
| Nitrogen | 80.0% by volume |
| Water steam | 2.7% by volume |
| Butane | 2.1% by volume |
| Carbon oxides | 3.0% by volume |

The oxidation reactions (with average conversion of 86% and average selectivity of 66%) take place in the longitudinal flow reactor (20).

The composition of the gas exiting the reactor (line 22) is as follows (typical values):

| | |
|---|---|
| Oxygen | 4.6% by volume |
| Nitrogen | 78.3% by volume |
| Water steam | 10.3% by volume |
| Butane | 0.3% by volume |
| Carbon oxides | 5.3% by volume |
| Maleic anhydride | 1.2% by volume |
| Organic by-products | traces |

After cooling in unit (24), the effluents are fed to a column (26) where the maleic anhydride is absorbed by a selective organic solvent (here, dibutyl phthalate is used). The maleic anhydride recovered from the solvent (line 30) is 3,100 Kg/h. The exhaust gas (32) exiting the absorber is 74141 Kg/h. 45% of exhaust gases i.e. 33,364 Kg/h, is conveyed to the incinerator (34). The remaining fraction (40) i.e. 40,777 Kg/h, is conveyed to a water-scrubbing column (42) where water-soluble organic compounds are removed and excess water produced by the reaction is condensed by cooling.

The scrubbing column effluent (line 38) is fed as recycle product to the second compression stage suction.

The recycle current is 38,720 Kg/h; its typical composition is:

| | |
|---|---|
| Oxygen | 5.1% by volume |
| Nitrogen | 86.1% by volume |
| Steam water | 2.7% by volume |
| Butane | 0.3% by volume |
| Carbon oxides | 5.8% by volume |
| Totally, the following rates are obtained: | |
| Maleic anhydride produced | 3,100 Kg/h |
| Butane fed | 3,008 Kg/h |

| | |
|---|---|
| Yield | 1.03 Kg/Kg |
| Compression power | 2,264 Kw |
| Gas conveyed to incinerator | 33,364 Kg/h |

EXAMPLE 2

With reference to FIG. 1 annexed hereto, the process without gas recycling is as follows:

74,868 Kg/h air are fed (line 10) to first compression stage suction (11).

Air is compressed through two compression stages (11 and 13) to a 3.55 bar pressure, subsequently mixed with 3,289 Kg/h of n-butane feed (line 16).

The total mixture (18) is the feed to the reactor (20).
The feed is 78,157 Kg/h and consists of:

| | |
|---|---|
| Oxygen | 20.0% by volume |
| Nitrogen | 75.1% by volume |
| Water steam | 2.8% by volume |
| Butane | 2.1% by volume |

The oxidation reactions (with average conversion of 86.5% and average selectivity of 65%) take place in the longitudinal flow reactor.

The composition of the gas exiting the reactor (line 22) is as follows (typical values):

| | |
|---|---|
| Oxygen | 12.1% by volume |
| Nitrogen | 73.4% by volume |
| Water steam | 10.5% by volume |
| Butane | 0.3% by volume |
| Carbon oxides | 2.5% by volume |
| Maleic anhydride | 1.2% by volume |
| Organic by-products | traces |

After cooling, the effluents (22) are fed to a column (26) where the maleic anhydride is absorbed by a selective organic solvent (same as in Example 1).

The maleic anhydride recovered from the solvent (line 30) is 3,100 Kg/h.

The exhaust gas exiting the absorber (32) is 75,057 Kg/h. The entire amount is conveyed to the incinerator (34).
Totally, the following rates are obtained:

| | |
|---|---|
| Maleic anhydride produced | 3,100 Kg/h |
| Butane fed | 3,289 Kg/h |
| Yield | 0.94 Kg/Kg |
| Compression power | 3,283 Kw |
| Gas conveyed to incinerator | 75,057 Kg/h |

The advantages offered by the process in this invention are evidenced by comparing the two examples; in particular, the following is obtained:

a) Reduced consumption of butane, about 90 Kg per ton of maleic anhydride produced.

b) Reduced consumption of electric power, about 330 Kwh per ton of maleic anhydride produced.

b) Remarkable reduction in gas conveyed to incineration (about 45% over the amount in the traditional technique).

We claim:

1. Process for the production of maleic anhydride by catalytic oxidation of n-butane in the vapor phase, comprising the steps of:

compressing air, oxygen-enriched air or oxygen to a pressure of 1.21 to 3.04 bar;

mixing said air, oxygen-enriched air or oxygen with recovered exhaust gas to form a recycle gaseous stream;

compressing said recycle gaseous stream to a pressure of 2.03 to 6.08 bar to form a compressed recycle gaseous stream;

mixing said compressed recycle gaseous stream with a butane feed to form a reaction mixture at a pressure of 2.03 to 6.08 bar;

the percentage of exhaust gas in said recycle gaseous stream being regulated such that said reaction mixture has an oxygen content of from 10% to 18% by volume, and the amount of butane being regulated such that the total butane concentration in said reaction mixture ranges from 1.6% to 3.0% by volume;

feeding said reaction mixture to an oxidation reactor where said butane is catalytically reacted to produce maleic anhydride and other reaction gases comprising nitrogen, oxygen, non-converted butane, organic by-products and water steam;

cooling said maleic anhydride and other reaction gases;

feeding said maleic anhydride and other reaction gases to an absorber containing an absorption medium selected from the group consisting of water and an organic solvent to recover said maleic anhydride and produce an exhaust gas fraction, said absorber operating at an outlet pressure of 1.21 to 3.04 bar;

water-scrubbing said exhaust gas fraction to remove all organic compounds except non-converted butane to produce said recycle gaseous stream and a remaining exhaust gas fraction;

conveying said remaining exhaust gas fraction to an incinerator where butane and organic products in the remaining exhaust gas fraction are burnt to produce water and carbon dioxide.

2. A process according to claim 1, wherein said recycle gaseous stream is conveyed to a compressor.

3. A process according to claim 1, wherein said oxidation reactor is selected from the group consisting of a fixed-bed reactor and a fluidized bed reactor.

4. A process according to claim 1, wherein said organic solvent is selected from diesters of phthalic acid.

5. A process according to claim 4, wherein said diesters of phthalic acid are selected from the group consisting of dibutyl phthalate and dioctyl phthalate.

6. A process according to claim 1, wherein the catalytic reaction is carried out at a reaction temperature of 370°–449° C.

7. A process according to claim 6, wherein said reaction temperature is 400° C.

8. A process according to claim 1, wherein said reaction mixture is fed to an inlet of said oxidation reactor at an inlet pressure of 2.03–6.08 bar.

9. A process according to claim 8, wherein said reactor inlet pressure is 3.44 bar.

10. A process according to claim 1, wherein said oxygen content is from 11 to 16% by volume.

11. A process according to claim 1, wherein said catalytic reaction is carried out at a space velocity of 1000–3000 $h^{-1}$.

12. A process according to claim 11, wherein said space velocity is 1500 $h^{-1}$.

13. A process according to claim 1, wherein said total butane concentration in the reaction mixture is 2.1% by volume.

* * * * *